US 9,238,110 B2

(12) United States Patent
Davies et al.

(10) Patent No.: US 9,238,110 B2
(45) Date of Patent: Jan. 19, 2016

(54) MEDICATED MODULE HAVING A COLLAPSIBLE FEATURE

(75) Inventors: James Alexander Davies, Warwickshire (GB); Steven Wimpenny, Warwickshire (GB); Daniel Thomas De Sausmarez Lintell, Warwickshire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 330 days.

(21) Appl. No.: 13/883,185

(22) PCT Filed: Oct. 31, 2011

(86) PCT No.: PCT/EP2011/069102
§ 371 (c)(1),
(2), (4) Date: May 2, 2013

(87) PCT Pub. No.: WO2012/059455
PCT Pub. Date: May 10, 2012

(65) Prior Publication Data
US 2013/0226143 A1 Aug. 29, 2013

Related U.S. Application Data

(60) Provisional application No. 61/432,695, filed on Jan. 14, 2011.

(30) Foreign Application Priority Data

Nov. 3, 2010 (EP) .................................... 10189789

(51) Int. Cl.
*A61M 5/50* (2006.01)
*A61M 5/315* (2006.01)
(Continued)

(52) U.S. Cl.
CPC ......... *A61M 5/31596* (2013.01); *A61M 5/2425* (2013.01); *A61M 5/2429* (2013.01);
(Continued)

(58) Field of Classification Search
CPC .......... A61M 5/31596; A61M 5/2448; A61M 5/2459; A61M 5/3146; A61M 2005/1787; A61M 5/2429; A61M 5/2425
See application file for complete search history.

(56) References Cited

U.S. PATENT DOCUMENTS 3,892,237 A * 7/1975 Steiner .......................... 604/200
5,637,087 A * 6/1997 O'Neil et al. .................... 604/82
(Continued)

FOREIGN PATENT DOCUMENTS

| JP | H08238324 A | 9/1996 |
|----|-------------|--------|
| JP | 200441568 A | 2/2004 |

(Continued)

OTHER PUBLICATIONS

Machine Translation of 88/02265 A1.
(Continued)

*Primary Examiner* — Nathan R Price
*Assistant Examiner* — Melissa A Snyder
(74) *Attorney, Agent, or Firm* — McDonnell Boehnen Hulbert & Berghoff LLP (57) ABSTRACT

A system and method for priming a medicated module during attachment of the medicated module to a drug delivery device. The drug delivery device has a drug reservoir holding a first medicament. The medicated module includes an upper retention feature and a lower retention feature, wherein the upper retention feature is axially moveable relative to the lower retention feature. The medicated module also includes an engagement needle and an output needle, wherein the output needle is in fluid communication with the engagement needle. The module also includes a collapsible feature holding a second medicament, wherein the collapsible feature is operably connected to the upper retention feature. During attachment to the drug delivery device, (i) the upper retention feature moves axially relative to the lower retention feature, (ii) the collapsible feature collapses, and (iii) the engagement needle and the output needle are primed with the second medicament.

11 Claims, 5 Drawing Sheets

(51) Int. Cl.
  *A61M 5/24*  (2006.01)
  *A61M 5/32*  (2006.01)
  *A61M 5/31*  (2006.01)
  *A61M 5/34*  (2006.01)
  *A61M 5/178*  (2006.01)

(52) U.S. Cl.
  CPC ........... *A61M5/2448* (2013.01); *A61M 5/3294* (2013.01); *A61M 5/2466* (2013.01); *A61M 5/3146* (2013.01); *A61M 5/347* (2013.01); *A61M 5/50* (2013.01); *A61M 5/5086* (2013.01); *A61M 2005/1787* (2013.01); *A61M 2005/3247* (2013.01)

(56) References Cited

U.S. PATENT DOCUMENTS

| 6,315,761 | B1 | 11/2001 | Shcherbina et al. | |
| 6,562,002 | B1 | 5/2003 | Taylor | |
| 6,723,074 | B1 * | 4/2004 | Halseth | 604/201 |
| 7,981,081 | B2 | 7/2011 | Marsh et al. | |
| 8,753,319 | B2 * | 6/2014 | Davies et al. | 604/191 |
| 2006/0229562 | A1 | 10/2006 | Marsh et al. | |
| 2006/0276755 | A1 | 12/2006 | Sullivan et al. | |

FOREIGN PATENT DOCUMENTS

| JP | 2008535636 A | 9/2008 |
| WO | 8802265 A1 | 4/1988 |

OTHER PUBLICATIONS

Form PCT/IPEA/416, Notification of Transmittal of the International Preliminary Report on Patentability.

English Translation of Notice of Reasons for Rejection issued in Japanese Patent Application No. 2013-537100 dated Sep. 8, 2015.

\* cited by examiner

MEDICATED MODULE HAVING A COLLAPSIBLE FEATURE

CROSS REFERENCE TO RELATED APPLICATIONS

The present application is a U.S. National Phase Application pursuant to 35 U.S.C. §371 of International Application No. PCT/EP2011/069102 filed Oct. 31, 2011, which claims priority to European Patent Application No. 10189789.0 filed Nov. 3, 2010 and U.S. Provisional Patent Application No. 61/432,695 filed Jan. 14, 2011. The entire disclosure contents of these applications are herewith incorporated by reference into the present application.

FIELD OF INVENTION

This present patent application relates to medical devices and methods of delivering at least two drug agents from separate reservoirs using devices having only a single dose setting mechanism and a single dispense interface. A single delivery procedure initiated by the user causes a non-user settable dose of a second drug agent and a variable set dose of a first drug agent to be delivered to the patient. The drug agents may be available in two or more reservoirs, containers or packages, each containing independent (single drug compound) or pre-mixed (co-formulated multiple drug compounds) drug agents. Specifically, this application concerns a method and system for priming a medicated module during attachment of the medicated module to a primary drug delivery device.

BACKGROUND

Certain disease states require treatment using one or more different medicaments. Some drug compounds need to be delivered in a specific relationship with each other in order to deliver the optimum therapeutic dose. The presently proposed devices and methods are of particular benefit where combination therapy is desirable, but not possible in a single formulation for reasons such as, but not limited to, stability, compromised therapeutic performance and toxicology.

For example, in some cases it might be beneficial to treat a diabetic with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems when delivering two active medicaments or "agents" simultaneously. The two active agents may interact with each other during the long-term, shelf life storage of the formulation. Therefore, it is advantageous to store the active components separately and combine them at the point of delivery, e.g. injection, needle-less injection, pumps, or inhalation. However, the process for combining the two agents needs to be simple and convenient for the user to perform reliably, repeatedly and safely.

A further problem is that the quantities and/or proportions of each active agent making up the combination therapy may need to be varied for each user or at different stages of their therapy. For example one or more active agents may require a titration period to gradually introduce a patient up to a "maintenance" dose. A further example would be if one active agent requires a non-adjustable fixed dose while the other is varied in response to a patient's symptoms or physical condition. This problem means that pre-mixed formulations of multiple active agents may not be suitable as these pre-mixed formulations would have a fixed ratio of the active components, which could not be varied by the healthcare professional or user.

Additional problems arise where a multi-drug compound therapy is required, because many users cannot cope with having to use more than one drug delivery system or make the necessary accurate calculation of the required dose combination. This is especially true for users with dexterity or computational difficulties. Further, in some circumstances, it is also necessary to perform a priming procedure of the device and/or needle cannulae before dispensing the medicaments. The priming procedure may be used to remove air from the device and/or needle cannulae before dispensing the medicaments. Still further, for some drug combinations for which this delivery of two medicaments in a single injection step is desirable, it may be additionally desirable for the two medicaments to be delivered substantially sequentially (i.e., one after the other, with minimal or no opportunity for mixing). Additional issues may arise due to the ullage volume that may be left in a drug delivery device post dispense. For instance, a large ullage volume may result in a large volume of "wasted medicament.

Accordingly, there exists a need to provide devices and methods for the sequential delivery of two or more medicaments in a single injection or delivery step that is easy and straightforward for the user to perform. Further, there exists a need for such a device to be capable of being primed prior to the delivery of the medicaments.

The presently proposed devices and methods overcome the above-mentioned potential problems by providing separate storage containers for two or more active drug agents (e.g., a primary medicament and a secondary medicament). Specifically, a medicated module holds a secondary medicament and is configured to allow priming of a drug delivery system when the medicated module is attached to a primary drug delivery device. The medicated module may comprise enough of the secondary medicament to prime a needle assembly attached to the medicated module. After the medicated module is attached to the primary drug delivery device, the drug agents are then delivered to the patient during a single delivery procedure. Beneficially, the second medicament from the medicated module and the first medicament from the drug delivery device are delivered to the patient sequentially or substantially sequentially.

The proposed devices and methods also give the opportunity for varying the quantity of one or both medicaments. For example, one fluid quantity can be varied by changing the properties of the injection device (e.g. dialing a user variable dose or changing the device's "fixed" dose). The second fluid quantity can be changed by manufacturing a variety of secondary drug containing packages with each variant containing a different volume and/or concentration of the second active agent. The user or healthcare professional would then select the most appropriate secondary package or series or combination of series of different packages for a particular treatment regime. The proposed medicated module contains a self-contained collapsible reservoir in which non-user-settable dose of a medicament may be stored.

These and other advantages will become evident from the following more detailed description of the invention.

SUMMARY

The presently proposed devices and methods allow for complex combinations of multiple drug compounds within a single drug delivery system. The presently proposed devices and methods allow the user to set and dispense a multi-drug compound device through one single dose setting mechanism and a single dispense interface. This single dose setter controls the mechanism of the device such that a predefined combination of the individual drug compounds is delivered when a single dose of one of the medicaments is set and dispensed through the single dispense interface. Further, the medicated module of the drug delivery system is configured so that the medicated module is automatically primed during attachment to the primary drug delivery device.

By defining the therapeutic relationship between the individual drug compounds, the proposed delivery device and delivery methods help ensure that a patient/user receives the optimum therapeutic combination dose from a multi-drug compound device without the inherent risks associated with multiple inputs where the user has to calculate and set the correct dose combination every time they use the device. The medicaments can be fluids, defined herein as liquids or gases or powders that are capable of flowing and that change shape at a steady rate when acted upon by a force tending to change its shape.

Applicants' proposed concept is of particular benefit to users with dexterity or computational difficulties as the single input and associated predefined therapeutic profile removes the need for them to calculate their prescribed dose when they use the device and the single input allows considerably easier setting and dispensing of the combined compounds.

In a preferred embodiment a master drug compound, such as insulin, contained within a multiple dose, user selectable device could be used with a single use, user replaceable, module that contains a single dose of a secondary medicament and the single dispense interface. When connected to the primary device, the secondary compound is activated/delivered on dispense of the primary compound. Although the present application specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with our invention.

For the purposes of Applicants' disclosure the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys- Asn-Gly-Gly-Pro-Ser-Ser-Gly-Ala-Pro-Pro-Pro-Ser-NH2), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser -Lys-Lys-Lys-Lys-Lys-Lys-NH2).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

According to an embodiment, a medicated module is attachable to a drug delivery device, the drug delivery device having a drug reservoir holding a first medicament. The medicated module includes an upper retention feature and a lower retention feature, wherein the upper retention feature is axially moveable relative to the lower retention feature. The medicated module further includes an engagement needle and an output needle, wherein the output needle is in fluid communication with the engagement needle. Still further, the medicated module includes a collapsible feature holding a second medicament, wherein the collapsible feature is operably connected to the upper retention feature. During attachment to the drug delivery device, (i) the upper retention feature moves axially relative to the lower retention feature, (ii) the collapsible feature is compressed due to the axial movement, and (iii) the engagement needle and the output needle are primed with the second medicament.

When the medicated module is attached to the drug delivery device, (i) the upper retention feature moves axially relative to the lower retention feature, (ii) the collapsible feature is compressed due to the axial movement, and (iii) the engagement needle and the output needle are primed with the second medicament.

According to another embodiment, a medicated module attachable to a drug delivery device includes an upper retention feature and a lower retention feature, wherein the upper retention feature is axially moveable relative to the lower retention feature. The medicated module further includes an engagement needle and an output needle, wherein the output needle is in fluid communication with the engagement needle. Still further, the medicated module includes a piston in sliding fluid-tight engagement with a portion of the upper retention feature, wherein the piston and the portion of the upper retention feature form a cavity. This cavity comprises a second medicament. During attachment to the drug delivery device, (i) the upper retention feature moves axially relative to the lower retention feature, (ii) the engagement needle pierces the piston, (iii) the piston moves axially to decrease a size of the cavity, and (iv) the engagement needle and the output needle are primed with the second medicament. Other embodiments include a drug delivery system that includes such drug delivery devices and such medicated modules.

When the medicated module is attached to the drug delivery device, (i) the upper retention feature moves axially relative to the lower retention feature, (ii) the engagement needle pierces the piston, (iii) the piston moves axially to decrease a size of the cavity, and (iv) the engagement needle and the output needle are primed with the second medicament.

According to another embodiment, a medicated module attachable to a drug delivery device includes an upper retention feature and a lower retention feature, wherein the upper retention feature is axially moveable relative to the lower retention feature. The medicated module further includes an engagement needle and an output needle, wherein the output needle is in fluid communication with the engagement needle. Still further, the medicated module includes a reservoir holding a second medicament. The reservoir may be a collapsible feature holding a second medicament. The collapsible feature may be operably connected to the upper retention feature.

According to another embodiment, a medicated module attachable to a drug delivery device includes an upper retention feature and a lower retention feature, wherein the upper retention feature is axially moveable relative to the lower retention feature. The medicated module further includes an engagement needle and an output needle, wherein the output needle is in fluid communication with the engagement needle. Still further, the medicated module includes a reservoir holding a second medicament. The reservoir may be a cavity comprising the second medicament. The cavity may be operably connected to the upper retention feature. A piston in sliding fluid-tight engagement with a portion of the upper retention feature may form the cavity.

Alternatively, a second medicament may be contained in a cavity in the upper retention feature or with a vial, wherein the second medicament is retained by a piston in a volume in the cavity or vial.

According to yet another embodiment, a method of priming a medicated module is provided. The method includes providing a medicated module attachable to a drug delivery device. The drug delivery device comprises a reservoir having a primary medicament. The medicated module comprises (i) and engagement needle, (ii) and output needle, and (iii) a collapsible reservoir containing a secondary medicament, wherein the engagement needle and the output needle are in fluid communication. The method further includes attaching the medicated module to the drug delivery device and establishing fluid communication between the engagement needle and the collapsible reservoir during the attachment of the medicated module to the drug delivery device. The method also includes forcing the collapsible reservoir to collapse during attachment of the medicated module to the drug delivery device, wherein during the collapse, the engagement needle and the output needle of the medicated module are primed with the secondary medicament. The engagement needle and the output needle of the medicated module are filled with the secondary medicament, hence removing the air.

The medicated module can be designed for use with drug delivery devices having an appropriate interface. However, it may be preferable to design the module in such a way as to limit its use to one exclusive primary drug delivery device (or family of devices) through employment of dedicated or coded features to prevent attachment of a non-appropriate medicated module to a non-matching device. In some situations it may be beneficial to ensure that the medicated module is exclusive to one drug delivery device while also permitting the attachment of a standard drug dispense interface to the device. This would allow the user to deliver a combined therapy when the module is attached, but would also allow delivery of the primary compound independently through a standard drug dispense interface in situations, such as, but not limited to, dose splitting or top-up of the primary compound.

A particular benefit of Applicants' method and system is that the method and system allow a user to prime the output needle during attachment of a medicated module to a drug delivery device. Additionally, a medicated module in accordance with Applicants' proposed concept provides a fluid-tight seal for a medicament prior to attachment to a drug delivery device. Beneficially, the fluid-tight seal may reduce or prevent contamination of the medicament.

Another benefit of Applicants' methods and systems is that the methods and systems serve to limit or minimize the amount of ullage left in the medicated module post administration (relative to the volume of the fixed dose of medicament in the module). Further, in given embodiments, Applicants' method and systems allow for sequential dosing of a first medicament and a second medicament through a single dispense interface. Thus, the methods and systems beneficially prevent or limit mixing of the first, primary medicament and the second medicament. This may be beneficial, for example, when mixing of medicaments negatively or detrimentally affects at least one of the medicaments.

A medicated module according to the invention may comprise a reservoir holding a second medicament, an upper and a lower retention feature configured to be axially moveable relative towards each other, an engagement needle and an output needle in fluid communication with each other, wherein at least on of the needle may be fixed to the lower retention feature. When the medicated module is attached to a drug delivery device, the upper retention feature is moved axially relative to the lower retention feature and the engagement needle, the reservoir is compressed due to the axial movement, and at least one of the engagement needle and an output needle are primed with the second medicament.

In a preferred embodiment, the primary drug delivery device is used more than once and therefore is a multi-use device; however, the drug delivery device may also be a single use disposable device. Such a device may or may not have a replaceable reservoir of the primary drug compound, but the proposed concepts are equally applicable to both scenarios. It is also possible to have a suite of different medicated modules for various conditions that could be prescribed as one-off extra medication to patients already using a standard drug delivery device. Should the patient attempt to reuse a previously used medicated module, this module may include a locking needle guard that is activated after a user delivers a dose from the medicated module. Other means of alerting the user may include some (or all) of the following:

Physical prevention of medicated module re-attachment to the primary drug delivery device once the module has been used and removed.

Physical/hydraulic prevention of subsequent liquid flow through the drug dispense interface once it has been used. Physical locking of the dose setter and/or dose button of the primary drug delivery device.

Visual warnings (e.g. change in color and/or warning text/indicia within an indication window on the module once insertion and/or fluid flow has occurred).

Tactile feedback (presence or absence of tactile features on the outer surface of the module hub following use).

A further proposed feature is that both medicaments are delivered substantially sequentially via one injection needle and in one injection step. This offers a convenient benefit to the user in terms of reduced user steps compared to administering two separate injections. This convenience benefit may also result in improved compliance with the prescribed therapy, particularly for users who find injections unpleasant or who have computational or dexterity difficulties.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which.

DETAILED DESCRIPTION

Applicants' proposed concept is a system and method for priming a medicated module as the medicated module is attached to a primary drug delivery device. The proposed concept specifically relates to a medicated module that holds a secondary medicament and is configured to prime the medicated module with the secondary medicament during attachment to a primary drug delivery device.

Figure 1:
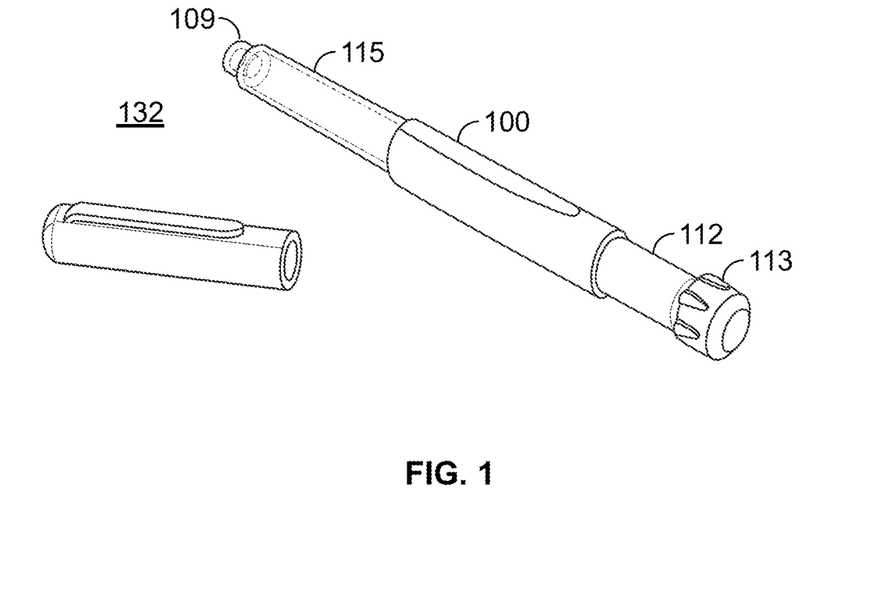
FIG. 1 illustrates a perspective view of one possible drug delivery device that can be used with Applicants' medicated module.

A medicated module in accordance with embodiments of Applicants' proposed concepts may be attached to a primary drug delivery device, such as drug delivery device 100. FIG. 1 illustrates one example of a drug delivery device 100 that a medicated module, such as the medicated module depicted in FIGS. 2-3, can be attached to the connection means 109 of distal end 132. Each medicated module is preferably self-contained and provided as a sealed and sterile disposable module that has an attachment means compatible to the attachment means 109 at the distal end 132 of device 100. Although not shown, the medicated module could be supplied by a manufacturer contained in a protective and sterile container, where the user would peel or rip open a seal or the container itself to gain access to the sterile medicated module. Further, the drug delivery device 100 includes a housing including a single dose setter 112. The dose setter 112 may be operably connected to a primary reservoir of medicament that may be stored in the drug delivery device, such as in cartridge holder 115. The user may use a dose dial button 113 in order to dial a user selectable dose of the primary medicament.

Figure 2:
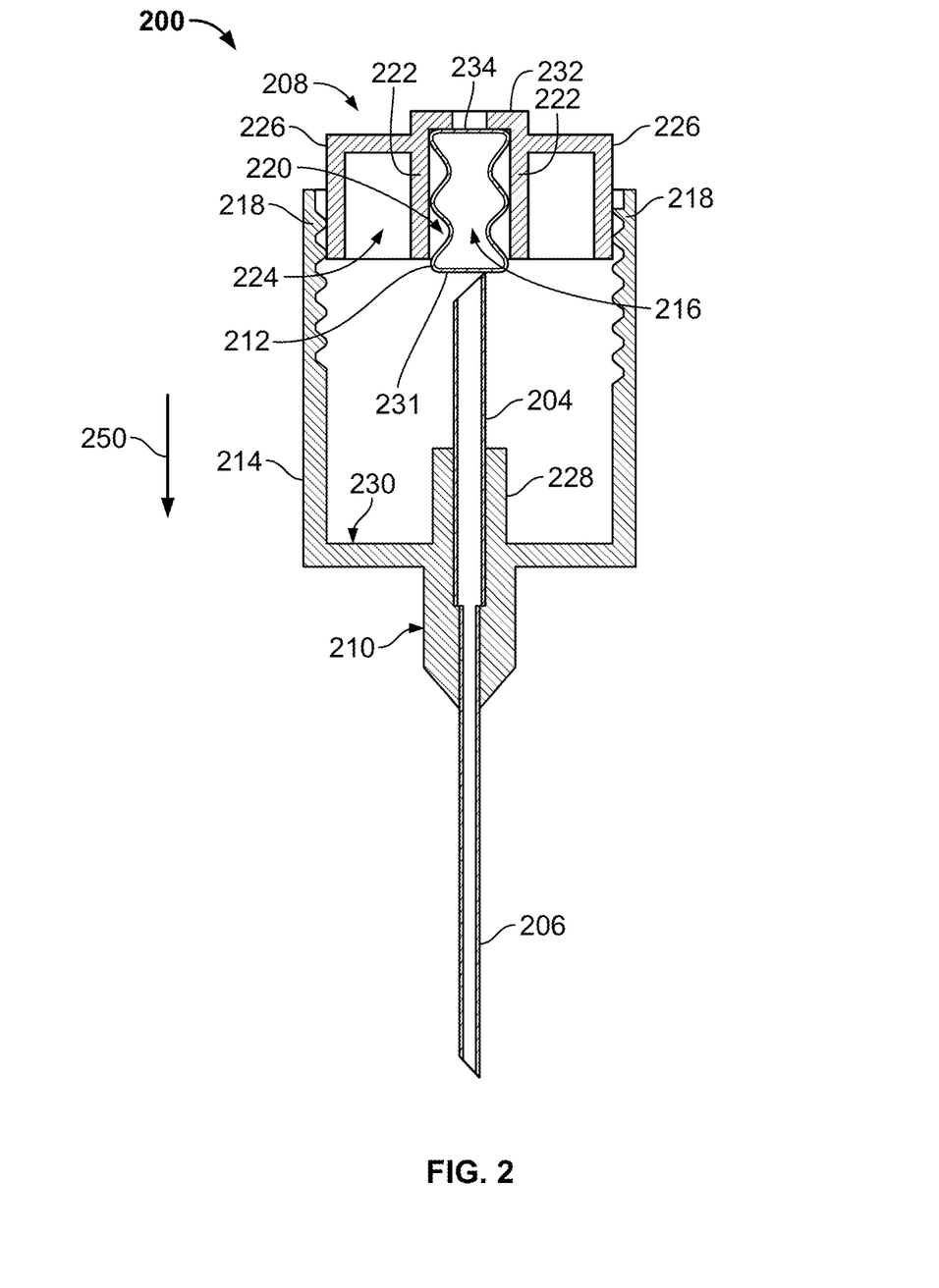
FIG. 2 illustrates a cross-sectional view of an exemplary medicated module.
Figure 3:
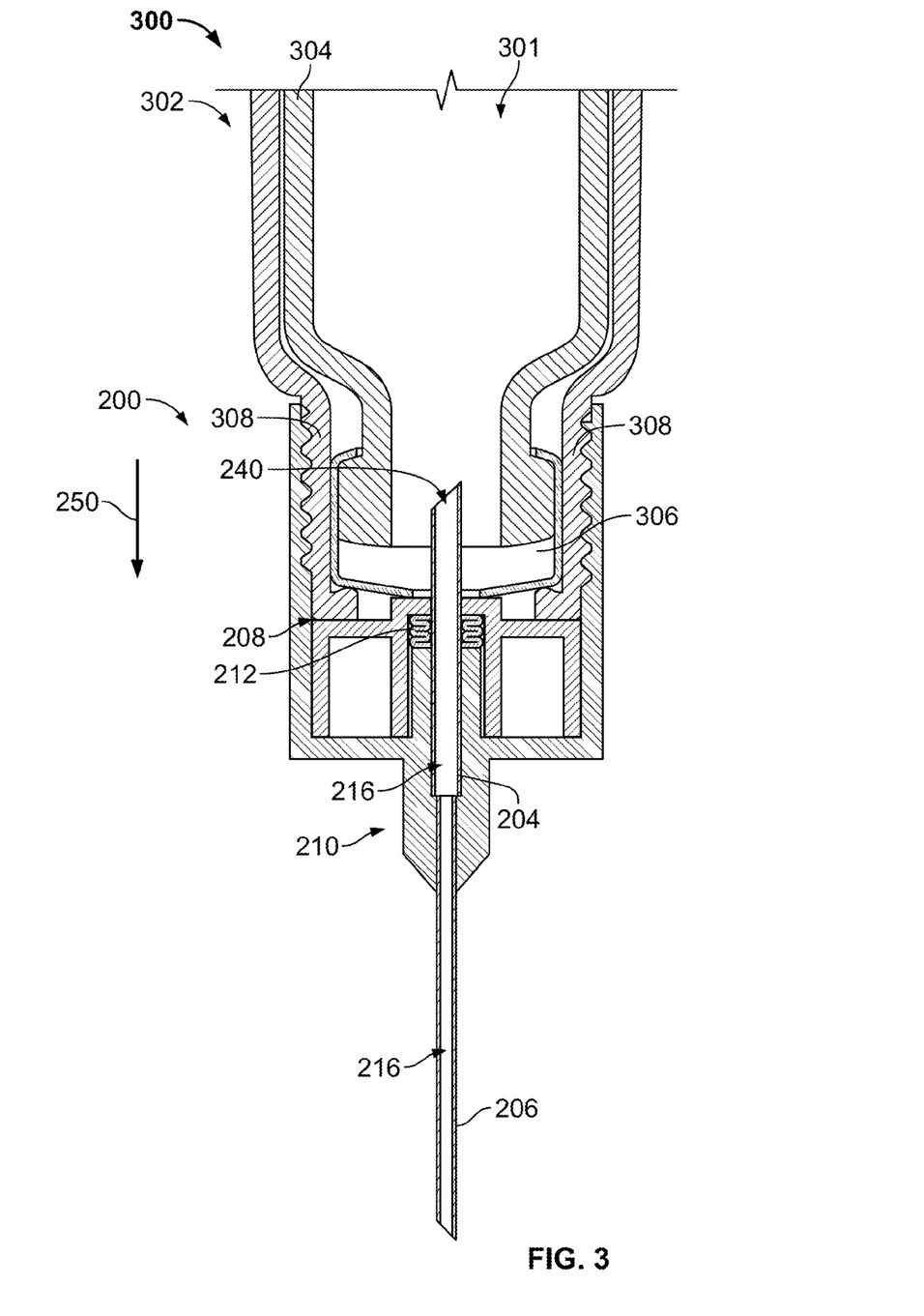
FIG. 3 illustrates a cross-sectional view of the exemplary medicated module of FIG. 2 attached to an exemplary drug delivery device.

Applicants' proposed concept is a medicated module that is automatically primed upon attachment to a primary drug delivery device. FIG. 2 illustrates a medicated module 200 in accordance with an embodiment of Applicants' proposed concept. Further, FIG. 3 illustrates a drug delivery system 300 that includes medicated module 200 attached to a drug delivery device 302 that holds a first, primary medicament 301. As will be described in detail below, medicated module 200 is primed as it is attached to drug delivery device 302.

The medicated module 200 includes a first needle cannula 204 and a second needle cannula 206. As shown in FIGS. 2 and 3, the first and second needles are in fluid communication with one another. The first needle 204 may be referred to herein as an "engagement needle", as the needle engages with or communicates with the reservoir 304 of drug delivery device 302 when the module 200 and device 302 are attached. Further, the second needle 206 may be referred to herein as an "output needle", as the second needle may be used to subcutaneously inject medicament into an injection site, such as an injection site of a user of drug delivery system 300. It should be noted that although the medicated module 200 is depicted as including two needles, the medicated module 200 may instead contain a single, double-ended needle having an engagement portion and an output portion. This single cannula could either be straight bored, or could have an enlarged section (produced by hydroforming, for example) at the proximal (inlet) end. A benefit of the enlarged section (formed either by having the 2 cannula in series as shown in FIG. 2, or as a single cannula with enlarged section) is that it would enable a larger volume of secondary medicament to be injected.

The medicated module 200 also includes an upper retention feature 208, a lower retention feature 210, and a collapsible feature 212. The collapsible feature 212 holds a medicament, such as secondary medicament 216. Example secondary medicaments include, but are not limited to GLP1 medications or pre-mix formulations of insulin and GLP1. To prevent the possible contamination of the medicament prior to use, the collapsible feature 212 may be a hermetically-sealed container that provides a fluid-tight seal. The collapsible feature may be composed of any suitable material capable of securely holding a medicament and collapsing or compressing under a pre-determined force, is additionally broadly inert when placed into long term contact with second medicament, and that offers good performance with respect to leachables and/or extractables. For example, the collapsible feature may be composed of; low-density polyethylene (LDPE) or linear low-density polyethylene (LLDPE). Alternative materials, including TPE (thermoplastic elastomer), liquid silicone rubber (LSR) and natural rubbers are also possible. Where improved barrier properties are desirable, laminate materials may be used e.g. multilayer materials consisting of the primary membrane material (potentially as above) plus additional thin layers of materials like PVC (polyvinyl chloride) PCTFE (polychlorotrifluoroethylene) or aluminum. Other materials and/or materials combinations are also possible.

The upper retention feature 208 is axially moveable relative to the body 214 of the medicated module. Further, in this example, lower retention cap or feature 210 is fixed, and thus the upper retention feature 208 is axially moveable relative to the lower retention cap 210. Still further, the lower retention feature 210 may act as a needle hub that retains the engagement needle 204 and the output needle 206, as shown in FIGS. 2-3. Therefore, the engagement needle 204 and the output needle 206 are fixed in the lower retention feature 210.

In this example, upper retention feature 208 includes a first cavity 220 defined by inner wall 222, and a second generally concentric cavity 224 defined by outer wall 226. The first cavity 220 and the second cavity 224 may be a variety of different shapes. Preferably, the cavities 220 and 224 are generally circular or annular in cross-section. However, the cavities may be any other suitable polygonal-shape, such as a square. Outer wall 226 may include features (not shown) that allow for axial movement along the body 214 of the medicated module 200. These features may interact with corresponding features (not shown) on the inner wall of body 214 of the medicated module 200 to allow for axial movement. Such features may typically consist of at least one axial protrusion that communicates with a corresponding axial slot on the mating component. The slot element might be formed as a recess or as a gap between two adjacent rib features (or similar configuration). Preferably the slot feature(s) will include bump features, one-way clip features or the like that help maintain the axial position of the upper retention feature relative to the lower retention cap until the medicated module is attached to the primary device. Additional features may also be preferably provided at or near the end of the axial travel in order to retain the upper retention feature in the module in-use/post-use axial position. Such features (e.g., a locking mechanism) would be preferably configured to prevent return of the upper retention feature to a pre-attachment axial position.

As shown in FIG. 2, the collapsible feature 212 is in contact with upper retention feature 208. Specifically, the collapsible feature 212 is located in the first cavity 220. The collapsible feature 212 may be operably connected to the upper retention feature 208. For instance, the proximal surface of the collapsible feature may be glued to the upper retention feature. Other types of connection, including interference/friction fits, are possible as well. Beneficially, during attachment to drug delivery device 300, inner wall 222 serves to control the compression of the collapsible member by confining the collapsible feature 212 to first cavity 220, as can be seen in FIG. 3 and which is described in more detail below.

The medicated module 200 also includes an attachment means 218. The attachment means 218 is configured to attach to a corresponding attachment means of a drug delivery device, such as the attachment means 308 of drug delivery device 302 (or, in another example, the attachment means 109 at the distal end 132 of device 100). Attachment means 308 is depicted as being a thread; however, this is intended as an example only and other attachment means are possible. Further, in an example embodiment, the medicated module 200 also includes a needle cover or needle guard (not shown). A needle cover may have a connection feature (e.g., a snap-fit feature) that allows the cover to be removably attached to the body of the medicated module 200. A needle cover or needle guard may substantially conceal the output needle 206 from a user's view so as to beneficially reduce any needle anxiety that a patient may be experiencing. While substantially concealing the needle, the needle cover or needle guard also helps to prevent inadvertent needle sticks.

Attachment of the medicated module 200 to drug delivery device 300 causes the collapsible member 212 containing the second medicament 216 to contact the top surface 232 of the upper retention cap 208. This contact in turn causes the upper retention feature 208 to be displaced axially relative to the lower retention feature 210. As seen when comparing FIG. 2 to FIG. 3, during attachment, the upper retention feature 208 moves axially towards to lower retention feature 210 in direction 250.

During this axial displacement, the engagement needle 204, which protrudes above a lower surface of the lower retention feature 210 (i.e., distal internal surface 230), pierces the collapsible feature 212 after a first predetermined amount of axial displacement. Further displacement of the upper retention feature 208 and the collapsible feature 212 relative to the lower retention feature 210 causes the engagement needle 204 to traverse through the collapsible feature 212. This traversal primes at least a portion of the engagement needle 204 with the secondary medicament 216.

At a second predetermined amount of axial displacement, the protrusion 228 in the lower retention cap 210 contacts the lower surface 231 (i.e., distal end) of the collapsible feature 212, resulting in subsequent displacement compressing the collapsible feature 212 and forcing the secondary medicament 216 into the engagement needle 204. As seen in FIG. 3, protrusion 228 has a diameter such that it is less than the diameter of the first cavity 220 of the upper retention feature 208. Thus, the protrusion 228 can fit into the first cavity 220 during attachment and can serve to compress the collapsible feature 212. This compression further acts to prime the engagement needle 204 with medicament 216. Further, the compression of the collapsible feature 212 beneficially ensures minimal ullage of the medicament 216 when the collapsible member 212 is fully compressed. The substantially complete compression ensures that substantially all of the secondary medicament 216 stored in the collapsible feature flows out of the collapsible feature to the engagement needle 204 and/or the output needle 206.

At a third predetermined amount of axial displacement of the upper retention feature 208 relative to the lower retention feature 210, the fully primed needle 204 pierces the top surface 234 (i.e., proximal end) of the collapsible feature 212 and thereafter the septum 306 of the reservoir 304. Once the engagement needle 204 passes through the septum 306 of the cartridge 304, fluid connection is made between the first, primary medicament 301 and the output needle 206.

FIG. 3 depicts collapsible member 212 in a substantially fully compressed state. As shown in this Figure, the engagement needle 204 and output needle 206 are fully primed with medicament 216. In order to fully prime the engagement needle 204 and the output needle 206, the collapsible feature 212 preferably holds at least enough secondary medicament 216 to fill the total volume of the engagement needle 204 and output needle 206. The enclosed volume of the combined cannula may preferably be less than the volume of liquid that will be primed from the collapsible member in order that at least a droplet of medicament is visible to a user on the end of the outlet needle 206 (to provide visual confirmation that the device has been primed).

After the module 200 is attached to the drug delivery device 302, a user may set a user-settable dose of the first medicament 301. The dose of the drug delivery device may be set in a usual manner (e.g., by dialing out an appropriate number of units of the primary medicament 301 with a dose dial of drug delivery device 302). Dispense of the second medicament 216 and the first medicament 301 may then be achieved via activation of the dosing mechanism of the drug delivery device.

As a user depresses a dosing button of the drug delivery device, the first medicament is forced in distal direction 250 toward the output needle 206. The first medicament 301 thereafter forces the second medicament 216 out output needle 206. After the second medicament 216 is forced from the output needle, subsequent depression of the dose button forces the dose of the first medicament 301 out of the output needle 206.

Beneficially, the second medicament 216 and the first medicament 301 are delivered substantially sequentially from medicated module 200. To help minimize the risk of mixing of the two medicaments within the medicated module, it is preferable for the diameter of the surface where the two liquids interact to be as small as possible, and similar in diameter to that of the outlet as this helps to ensure "plug flow" during delivery. In Applicants' proposed concept, the diameter of the surface where the two medicaments interact is sufficiently small to help ensure "plug flow." Specifically, the diameter of the surface where the two medicaments interact is limited to the diameter of the proximal end 240 of the engagement needle 204. Thus, due to plug flow, the second medicament 216 and first medicament 301 are delivered substantially sequentially. It should be understood, however, that some mixing of the two medicaments is possible during the substantially sequential delivery.

After the user finishes dispensing of the first and second medicaments 301, 216, the user may remove the output needle 206 from the injection site. Then, the depleted medicated module 200 may be disposed of. Assuming that the drug delivery device 302 still holds some first medicament 301, the drug delivery device 204 may be reused by the patient as required.

Figure 4A:
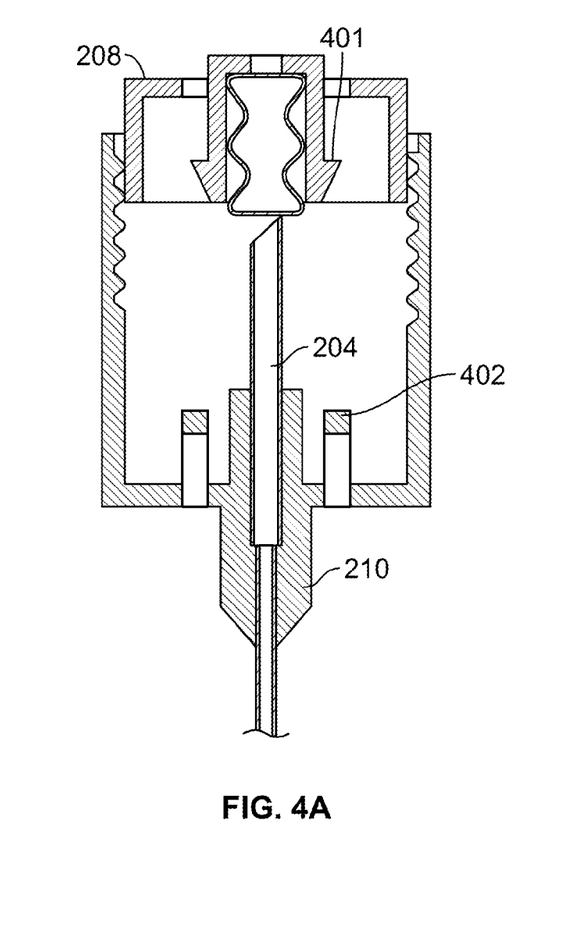
FIG. 4a illustrates a cross-sectional view of the exemplary medicated module prior to attachment to a drug delivery.
Figure 4B:
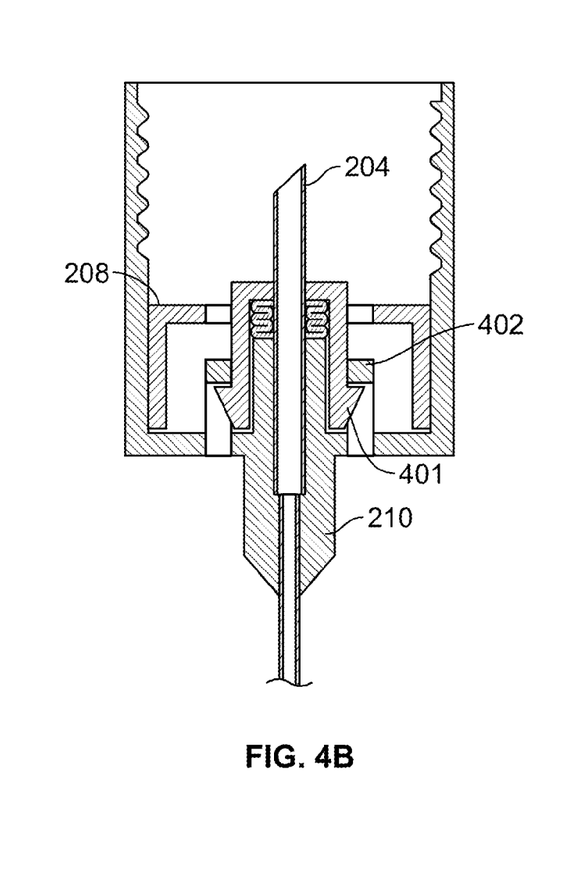
FIG. 4b illustrates a cross-sectional view of the exemplary medicated module of FIG. 4a after attachment to a drug delivery device.

In given embodiments, a locking mechanism may be included in the medicated module that retains the collapsible feature 212 in its compressed state after the module has been used to deliver medicament. That is, such a locking mechanism may keep collapsible feature 212 collapsed and prevent it from expanding to its pre-dispense position. Such a locking mechanism may be formed through the use of clip features 401 and 402 on the upper retention and lower retention features 208 and 210 respectively. These clip features may be preferably configured to only permit one-way axial movement between the two components, as shown in FIGS. 4a and 4b. Such a locking mechanism may permit reuse of the needle sub-assembly by a user a second time in instances where the fixed dose of the secondary medicament (i.e., second medicament 216) is not required. Example scenarios where this might be desirable include, but are not limited to, instances where a patient may need to or may wish to split their dose into two or more smaller doses. One example of a particular use scenario where this might be the case is at the end of life of the multi-use drug delivery device where the full dose of the primary medicament may not be available/remaining in the drug cartridge contained within the drug delivery device. In this instance a patient may elect to take the residual dose from the "old" device and then the remainder of the required dose from a new device, in which case reusing the medicated module a second time (rather than attaching a new, unused one) would prevent a patient from receiving a second dose of the secondary medicament. Beneficially, retaining the collapsible feature in its collapsed state may limit or prevent excessive ullage in the medicated module after use.

A medicated module in accordance with Applicants' proposed concept may also include features to encourage or ensure single-use of the medicated module. Such features may include a lock-out feature that locks out the needle or a feature that prevents reattachment to another drug delivery device. Alternatively, features may be present that discourage subsequent dosing through the medicated module via other means. However, in given embodiments, such as an embodiment configured for a split dose scenario discussed above, the features of the medicated module to encourage or ensure single-use may preferably be configured to permit a one-time reuse of the medicated module.

Figure 5:
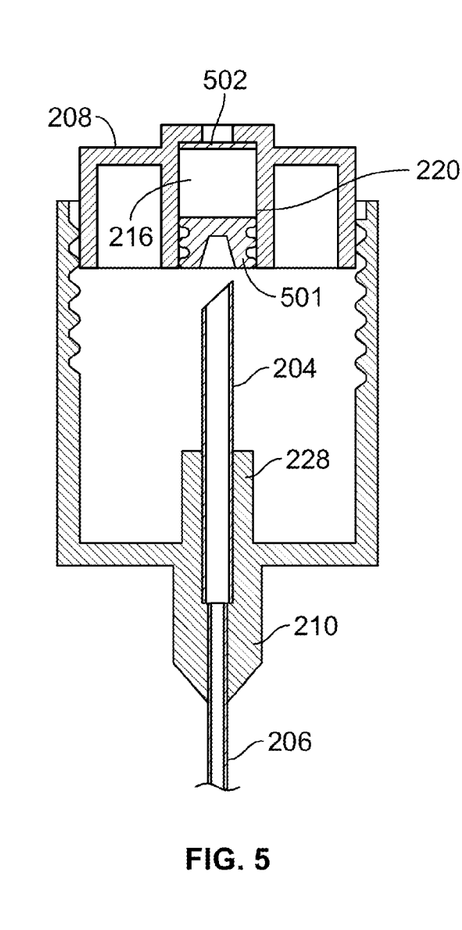
FIG. 5 illustrates a cross-sectional view of another exemplary medicated module of Applicant's medicated module before attachment to a drug delivery device.
Figure 6:
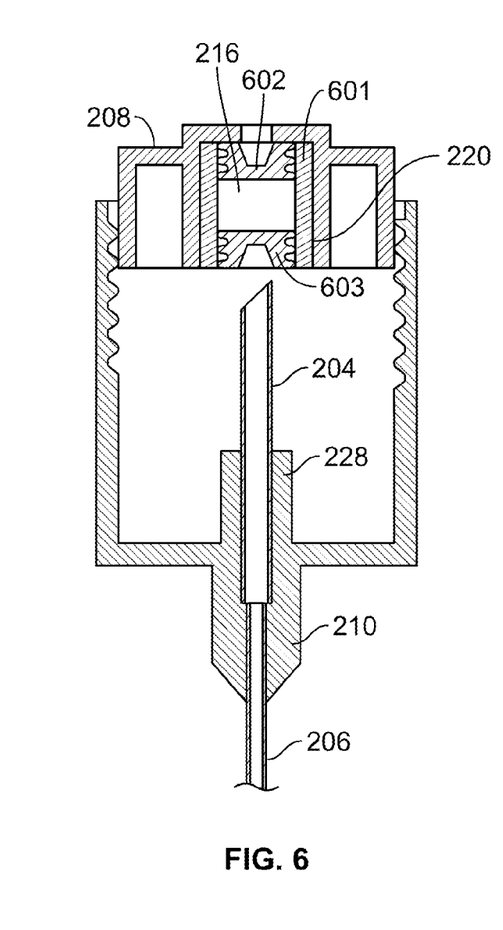
FIG. 6 illustrates a cross-sectional view of yet another exemplary medicated module of Applicant's medicated module before attachment to a drug delivery device.

In an alternative embodiment of Applicants' proposed concept, a piston arrangement may be used in lieu of a collapsible member in order to facilitate priming of the medicated module 200 during attachment to a primary drug delivery device. FIGS. 5 and 6 show two possible embodiments of such a piston design, each of which is shown in a pre-use condition. In FIG. 5 the second medicament 216 is contained within the cavity 220 in the upper retention feature 208 by use of a piston 501 at the distal end and closed at the proximal end with septum 502 that can be separate or co-molded with the cavity. In FIG. 6 the second medicament 216 is contained within a tube or vial 601 that can be manufactured with any medicament compatible material, such as glass or plastic. The medicament is contained within the vial 601 with a proximal septum or bung 602 and a sliding piston 603. Vial 601 can be retained within the cavity 220 by an adhesive, weld, press fit or any other means known to those skilled in the art. It should be explicitly noted, however, that many possibilities and permutations described above with respect to medicated module 200 may equally apply to medicated module 400.

Referring to FIG. 5, the secondary medicament 216 is contained within a cavity 220 formed between a portion of the upper retention feature 208) or cap (e.g., a cavity) and the piston 501. The piston 501 is in sliding fluid-tight engagement with an inner wall of the portion of the upper retention cap 208and thus provides a fluid-tight seal for the secondary medicament. Displacement of the lower retention cap relative to the upper retention cap, as described above in reference to the first embodiment, causes the engagement needle 204 to pierce the piston 251 and traverse through the medicament causing the needle to prime. At a second predetermined displacement, a protrusion 228 present in the lower retention cap 210 contacts the piston 251, which causes subsequent displacement to further act to prime the output and engagement needle 206, 204.

At a third predetermined displacement, the engagement needle 204 pierces the top surface of the upper retention feature 208, preferably through a septum or bung (see 502 in FIGS. 5 and 602 in FIG. 6) and the septum of the cartridge of the drug delivery device in the same manner as the first embodiment. Once the engagement needle 204 has passed through the septum of the cartridge fluid connection is made between the first medicament 301 and the engagement and output needle 204, 206. As before, the dose of the drug delivery device is then set in the normal manner (e.g. by dialling out the appropriate number of units). Dispense of the two medicaments is then achieved via activation of the multi-use device's dispensing mechanism.

After complete dispense of the second medicament 216, the output needle 206 can be removed from the injection site and the medicated module 200 disposed of, allowing the multi-use device to be reused by the patient as required.

Applicants' proposed concept also includes a method for priming a medicated module. The method includes providing a medicated module attachable to a drug delivery device. The drug delivery device comprises a reservoir having a primary medicament. The medicated module comprises (i) and engagement needle, (ii) and output needle, and (iii) a collapsible reservoir containing a secondary medicament, wherein the engagement needle and the output needle are in fluid communication. The method further includes attaching the medicated module to the drug delivery device and establishing fluid communication between the engagement needle and the collapsible reservoir during the attachment of the medicated module to the drug delivery device. The method also includes forcing the collapsible reservoir to collapse during attachment of the medicated module to the drug delivery device, wherein during the collapse, the engagement needle and the output needle of the medicated module are primed with the secondary medicament.

A medicated module in accordance with Applicants' proposed concept, such as medicated module 200 or medicated module 400, offers numerous advantages. For example, as described above, the medicated modules in accordance with Applicants' proposed concept are primed upon attachment to the primary drug delivery device. Since the device is primed upon attachment, a user may not need to take any additional action or steps to perform a priming action. This may be beneficial because, for example, in some situations, a user may forget to or neglect to perform a priming operation.

As another example, Applicants' proposed concept beneficially allows for sequential dosing of a secondary medicament stored in a medicated module followed by a primary medicament from a primary drug delivery device. The proposed medicated module limits the diameter of the surface where the primary medicament and secondary medicament interact relative to the outlet diameter, thus helping to ensure plug flow of the primary and secondary medicament. Thus, beneficially, the proposed concept prevents or limits the mixing of the two medicaments within the device. This could be beneficial for applications whereby the efficacy of the combined medication reduces over time and so it is best for the mixing to occur as close to in vivo as possible to maximum the therapeutic effect.

The connection or attachment between the medicated module of the herein described embodiments may contain additional features (not shown), such as connectors, stops, splines, ribs, grooves, and the like design features, that help to ensure that a specific medicated module or a specific set or kit of medicated modules are attachable only to a complementary or matching drug delivery device or devices. Such additional features would prevent the insertion of a non-appropriate medicated module to a non-matching injection device.

The shape of the medicated module may be a cylindrical body or any other geometric shape suitable for defining a fluid reservoir or for containing discrete self-contained reservoir of the medicament in the medicated module and for attaching one or more needle cannula. The medicated module can be manufactured from glass (as illustrated in FIG. 6) or other drug contact suitable material. The integrated output needle can be any needle cannula suitable for subcutaneous or intramuscular injection. Preferably the medicated module is provided by a drug manufacturer as a stand-alone and separate device that is sealed to preserve sterility. The sterile seal of the module is preferably designed to be opened automatically, e.g. by cutting, tearing or peeling, when the medicated module is advanced or attached to the drug delivery device by the user. A kit comprising a plurality of medicated modules may also be provided. Such a kit could comprise one or more medicated modules where each module has the same medicament, different medicaments, or different medicament concentrations.

The medicated module of Applicants' concept should be designed to operate in conjunction with a multiple use injection device, preferably a pen-type multi-dose injection device, similar to what is illustrated in FIG. 1. The injection device could be a reusable or disposable device. By disposable device it is meant an injection device that is obtained from the manufacturer preloaded with medicament and cannot be reloaded with new medicament after the initial medicament is exhausted. The device may be a fixed dose or a settable dose and preferably a multi-dose device, however, in some cases it may be beneficial to use a single dose, disposable device.

A typical injection device contains a cartridge or other reservoir of medication. This cartridge is typically cylindrical in shape and is usually manufactured in glass. The cartridge is sealed at one end with a rubber bung and at the other end by a rubber septum. The injection pen is designed to deliver multiple injections. The delivery mechanism is typically powered by a manual action of the user, however, the injection mechanism may also be powered by other means such as a spring, compressed gas or electrical energy.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A medicated module attachable to a drug delivery device, the drug delivery device having a drug reservoir holding a first medicament, the medicated module comprising:
   an upper retention feature;
   a lower retention feature, wherein the upper retention feature is axially moveable relative to the lower retention feature;
   attachment means provided at the lower retention feature for attachment of the module to the drug delivery device;
   an upper engagement needle;
   a lower output needle, wherein the output needle is in fluid communication with the engagement needle, wherein at least one of the output needle and the engagement needle is fixed to the lower retention feature; and
   a reservoir holding a second medicament, wherein the reservoir is operably connected to the upper retention feature and located upwardly from said engagement needle,
   wherein when the medicated module is attached to the drug delivery device,
   (i) at a first predetermined amount of axial displacement between the upper and lower retention feature, the upper retention feature is configured to move relatively towards the lower retention feature and the engagement needle such that fluid communication between the engagement needle and the reservoir is established, and
   (ii) at a second predetermined amount of axial displacement between the upper and lower retention feature, a protrusion provided by the lower retention feature contacts and compresses the reservoir,
   (iii) such that at least one of the engagement needle and the output needle is primed with the second medicament, and wherein, during dispense and after priming, substantially all the second medicament is dispensed before the first medicament is dispensed.

2. The medicated module of claim 1 wherein the reservoir comprises a collapsible feature holding the second medicament, wherein the collapsible feature is operably connected to the upper retention feature, and wherein in step (ii) the collapsible feature is compressed.

3. The medicated module of claim 2, wherein, during attachment, at the first predetermined amount of axial displacement between the upper and lower retention feature, the engagement needle pierces a distal end of the collapsible feature, thereby at least partially priming the engagement needle.

4. The medicated module of claim 3, wherein during attachment, at the second predetermined amount of axial displacement between the upper and lower retention feature, the protrusion contacts the distal end of the collapsible feature such that subsequent axial displacement between the upper and lower retention feature compresses the collapsible feature against the upper retention feature.

5. The medicated module of claim 4, wherein, at a third predetermined amount of axial displacement between the upper and lower retention feature when the engagement needle and the output needle are primed, a proximal end of the engagement needle pierces a proximal end of the collapsible feature.

6. The medicated module of claim 1, further comprising:
   a locking mechanism, wherein the locking mechanism prevents the collapsible feature from expanding to a pre-dispense position.

7. The medicated module of claim 1 wherein the reservoir comprises
   a piston in sliding fluid-tight engagement with a cavity in the upper retention feature or with a vial, wherein the second medicament is retained by the piston in a volume in the cavity or vial, and wherein, when the medicated module is attached to the drug delivery device, the engagement needle pierces the piston, and the piston is moved to decrease the volume of the cavity or vial.

8. The medicated module of claim 7, wherein, during attachment, at the first predetermined amount of axial displacement between the upper and lower retention feature, the engagement needle pierces the piston, thereby (i) establishing fluid communication between the engagement needle and the cavity and (ii) at least partially priming the engagement needle.

9. The medicated module of claim 8, wherein during attachment, at the second predetermined amount of axial displacement between the upper and lower retention feature, the protrusion contacts the piston such that subsequent axial displacement between the upper and lower retention feature forces the piston to move axially in a proximal direction.

10. The medicated module of claim 9, wherein, at a third predetermined amount of axial displacement between the upper and lower retention feature when the engagement needle and the output needle are primed, the engagement needle pierces a septum of the upper retention feature.

11. A method of priming the medicated module of claim 1, the method comprising:
   providing the medicated module;
   attaching the medicated module to the drug delivery device;
   establishing fluid communication between the engagement needle and the reservoir during the attachment of the medicated module to the drug delivery device; and
   forcing the reservoir to be compressed during attachment of the medicated module to the drug delivery device, wherein during the compression, medicament from the reservoir is transferred into the engagement needle and the output needle; and the engagement needle and the output needle of the medicated module are primed with the secondary medicament.

\* \* \* \* \*